(12) United States Patent
Wagner

(10) Patent No.: US 6,264,913 B1
(45) Date of Patent: Jul. 24, 2001

(54) NON-INVASIVE TEST FOR ASSESSING BACTERIAL OVERGROWTH OF THE SMALL INTESTINE

(75) Inventor: David A. Wagner, Nashua, NH (US)

(73) Assignee: Metabolic Solutions, Inc., Nashua, NH (US)

( * ) Notice: Subject to any disclaimer, the term of this patent is extended or adjusted under 35 U.S.C. 154(b) by 0 days.

(21) Appl. No.: 09/293,191

(22) Filed: Apr. 16, 1999

Related U.S. Application Data

(60) Provisional application No. 60/084,723, filed on May 8, 1998.

(51) Int. Cl.$^7$ ............... A61K 51/04; A61K 31/70; C12D 1/16
(52) U.S. Cl. ............ 424/1.37; 424/1.33; 424/1.65; 424/1.81; 424/1.13; 514/23; 514/24; 514/25; 435/24; 435/34; 435/35; 435/39
(58) Field of Search ................ 424/1.13, 1.33, 424/1.81, 1.65, 1.37; 435/29, 34, 35, 39; 514/23, 24, 25

(56) References Cited

U.S. PATENT DOCUMENTS 4,830,010 * 5/1989 Marshall ................ 128/630
5,458,910 * 10/1995 Gruetzmacher et al. ....... 426/611

OTHER PUBLICATIONS

Chang et al. Eur J Nucl Med; 22: 1118–1122, 1995.*
Rosenburg et al. Gastroenterology; 86: 1356, 1984.*
Martindale, the Extra Pharmacoppeia, p. 780, 1993.*
American Hospital Formulary Services, p. 1893, 1994.*
L.H. Adcock et al., The Metabolism of Sorbitol in the Human Subject,Journal Title Unknown,, vol. 65, p. 554–560, Aug. 13, 1956.

C.E. King et al., Small Intestine Bacterial Overgrowth, *Gastroenterology*, vol. 76, No. 5, p. 1035–1040, May 1979.

C.E. King et al., Comparison of the One–Gram d–[$^{14}$C] Xylose Breath Test to the [$^{14}$C]Bile Acid Breath Test in Patients with Small–Intestine Bacterial Overgrowth, *Digestive Diseases and Sciences*, vol. 25, No. 1, p. 53–58, Jan. 1980.

C.E. King et al., Comparison of the 1–Gram [$^{14}$C]Xylose, 10–Gram Lactulose–$H_2$, and 80–Gram Glucose–$H_2$, Breath Tests in Patients with Small Intestine Bacterial Overgrowth, *Gastroenterology*, vol. 91, No. 6, p. 1447–1451, 1986.

C.E. King et al., Detection of Small Intestine Bacterial Overgrowth by Means of a $^{14}$C–D–Xylose Breath Test, *Gastroenterology*, vol. 77, No. 1, p. 75–82, 1979.

N.W. Solomons et al., Application of a stable isotope ($^{13}$C)–labeled glycocholate breath test to diagnosis of bacterial overgrowth and ileal dysfunction, *J. Lab. Clin. Med.*, vol. 90, No. 3, p. 431–439, 1977.

P.P. Toskes et al., Xylose Catabolism in the Experimental Rat Blind Loop Syndrome, *Gastroenterology*, vol. 74, No. 4, p. 691–697, 1978.

S.M. Riordan et al., Factors Influencing the 1–g $^{14}$C–D–Xylose Breath Test for Bacterial Overgrowth, *The American Journal of Gastroenterology*, vol. 90, No. 9, p. 1445–1460, 1995.

* cited by examiner

Primary Examiner—Diana Dudash
Assistant Examiner—Shahnam Sharareh
(74) Attorney, Agent, or Firm—Jenkens & Gilchrist A Professional Corporation

(57) ABSTRACT

Provided herein is a novel breath test for assessing bacterial overgrowth. The test involves administration of a labeled sorbitol or sorbitol derivative to a subject and measurement of the label in breath and/or blood.

14 Claims, 1 Drawing Sheet

NON-INVASIVE TEST FOR ASSESSING BACTERIAL OVERGROWTH OF THE SMALL INTESTINE

RELATED APPLICATIONS

This application relates to prior Provisional Application Ser. No. 60/084,723, filed May 8, 1998.

BACKGROUND OF THE INVENTION

1. Field of the Invention

The present invention relates to a method for monitoring bacterial overgrowth of the small intestine. More specifically, the invention relates to administering labeled sorbitol or sorbitol derivatives to an individual and assessing labeled carbon dioxide in one or more specimens from the individual to determine bacterial overgrowth of the small intestine.

2. Description of the Prior Art

Normally, the human small intestine contains only small amounts of bacteria compared to the colon. Many structural or functional disorders of the gastrointestinal tract can lead to bacterial overgrowth of the small intestine. Small bowel bacterial overgrowth is characterized by steatorrhea (fat malabsorption), diarrhea, vitamin deficiencies, and carbohydrate malabsorption. Optimum care of patients with bacterial overgrowth requires adequate evaluation and proper antibiotic therapy. Unfortunately, bacterial overgrowth is difficult to diagnose with accuracy. Unlike many other illnesses, bacterial overgrowth is never cured but requires constant monitoring and therapy.

The current diagnostic "gold standard" for identifying small intestinal bacterial overgrowth is a quantitative culture of small bowel fluid aspirate. Jejunal fluid is collected through a small tube that is swallowed by the patient and positioned by a physician under fluoroscopic (x-ray) guidance. The jejunal fluid aspiration is cultured for the presence of bacteria. There are many limitations to this technique as a diagnostic test of small bowel bacterial overgrowth. These limitations include (1) discomfort of placing orointestinal tubes, (2) exposure to x-rays, (3) high medical costs (about $700) (4) culturing the aspirate is time consuming and (5) the poor diagnostic sensitivity of single aspirations.

The need for a reliable screening test for bacterial overgrowth fostered the development of non-invasive breath tests. These tests utilized radioactive $^{14}C$ and nonradioactive $^{13}C$ substrates, such as cholyl-$[^{14}C]$-glycine (bile acid breath test) and $^{14}C$ and $^{13}C$-xylose, or relied on bacterial metabolism of glucose or lactulose to evolve hydrogen gas in the breath. With the exception of the xylose breath test, all the other non-invasive screening tests have been shown to be unreliable to screen for bacterial overgrowth because of poor sensitivity and specificity of these tests. Recent clinical experience with the xylose breath test, however, has suggested a decrease in the sensitivity and specificity, perhaps due to the altered ability of intestinal bacteria to metabolize xylose.

These and other disadvantages of the prior art are overcome by the present invention. As shown herein, we provide a novel test for assessing bacterial overgrowth of the small intestine.

SUMMARY OF THE INVENTION

The present invention overcomes the limitations of the prior art and provides a method and kit for the assessment of bacterial overgrowth of the small intestine.

Provided herein is a method of assessing bacterial overgrowth of the small intestine in a subject comprising the steps of: a) administering to said subject an effective amount of carbon-labeled sorbitol or carbon-labeled sorbitol derivative to said subject; b) collecting expired breath from said subject; and c) measuring the amount of label in said expired breath to assess bacterial overgrowth of the small intestine in said subject. The label is a carbon label. Preferably the labeled compound administered is $^{13}C$ sorbitol or a $^{13}C$ sorbitol derivative, or mixtures thereof. Alternatively, the compound is $^{14}C$ sorbitol or a $^{14}C$ sorbitol derivative. The labeled sorbitol derivative is any sorbitol derivative that would be known to those skilled in the art and which would not be readily absorbed; thus, any increase in $CO_2$ enrichment would be due to bacteria rather than endogenous metabolism. The carbon-labeled compound may comprise a plurality of labeled carbons. Preferably, the sorbitol derivative is D-sorbitol, but L-sorbitol or a racemic mixture of the two also function.

In an alternative embodiment, provided herein is a method of assessing bacterial overgrowth of the small intestine in a subject comprising the steps of: a) administering to said subject an effective amount of carbon-labeled sorbitol or carbon-labeled sorbitol derivative to said subject; b) collecting blood from said subject; and c) measuring the amount of label in said blood to assess bacterial overgrowth of the small intestine in said subject.

The method further comprises comparing said amount of expired labeled carbon with a standard, whereby said comparing yields a measure of bacterial overgrowth of the small intestine. The standard comprises the mean value of expired label in a control population without bacterial overgrowth of the small intestine, or the mean value of expired label in a control population with bacterial overgrowth of the small intestine.

The label may be measured by techniques commonly used for measuring the presence of labeled species. Isotopic measurement of label is selected from the group consisting of mass spectrometric measurement, laser measurement, infrared detection, nuclear magnetic resonance and liquid scintillation counting of labeled carbon.

The present invention also provides a kit for assessing bacterial overgrowth of the small intestine comprising carbon-labeled sorbitol or carbon-labeled sorbitol derivative in a pharmaceutically acceptable carrier, and optionally a means for collecting expired breath and/or blood and/or blood treating agents.

The advantages of the present invention may be gleaned from the following detailed description.

DETAILED DESCRIPTION OF THE INVENTION

Figure 1:
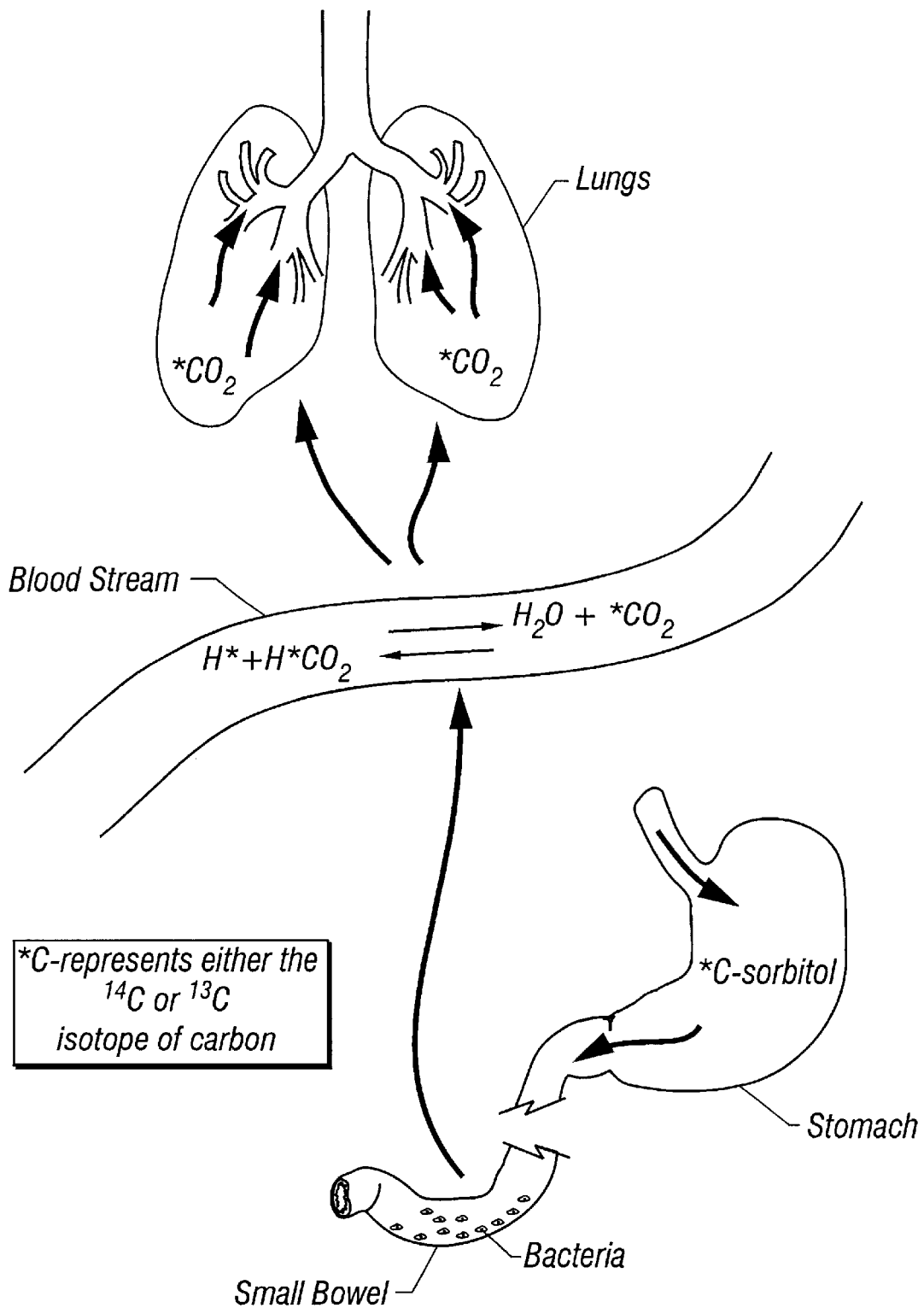
FIG. 1 shows the mechanism of action of the sorbitol test.

The sorbitol test is based on the ability of bacteria to metabolize this isotopically labeled substrate to produce labeled $CO_2$. Labeled $CO_2$ can then be detected as enrichment over baseline values in the breath or blood. Enrichment above an established threshold indicates an overabundance of the bacteria in the small bowel.

The method of the invention comprises administering one or more doses of a carbon-labeled compound to a subject. In the preferred embodiment, the carbon-labeled compound is sorbitol. In an additional embodiment, a carbon-labeled sorbitol derivative may be administered to the subject in one or more doses. Useful derivatives include, but are not limited to derivatives selected from the group consisting of polymers of sorbitol and mixtures thereof. As used herein, the term "compound" refers to labeled sorbitol or sorbitol derivative. The compound is oxidized in the patient, and a specimen is retrieved from the patient for analysis of labeled carbon dioxide. The specimen is of the type known to those skilled in the art which would contain labeled carbon dioxide. These include, but are not limited to breath or blood. The specimen from the patient is collected, and the amount of isotope in the specimen is analyzed. The amount of isotope determined is compared with the standard and this comparison yields a measure of bacterial overgrowth. Preferably, the compound is administered orally. If the compound is administered orally, it preferably is in a pharmaceutically acceptable carrier such as water or a sugar solution but may be delivered chemically bound to a peptide or similar entity and released upon digestion. In one embodiment of the present invention, a one or more breath samples are collected and analyzed. In an alternative embodiment, one or more blood samples are collected and analyzed.

The preferred labeled isotope is a carbon isotope which yields expired carbon dioxide. The preferred carbon isotopes are $^{13}$C and $^{14}$C. $^{13}$C is more preferred because it is a stable rather than a radioactive isotope.

Sorbitol or a sorbitol derivative having an isotope label at the 1-carbon position are preferred. This is because the 1-carbon is excised and exhaled as carbon dioxide at an early step in the oxidative process. However, in an alternative embodiment of the present invention, the compound may have a plurality of carbons labeled, for example, 1,2 $^{13}$C-sorbitol, 1,2,3 $^{13}$C-sorbitol, etc. to improve sensitivity. If a $^{13}$C isotope is used, the preferred method of measurement is with a mass spectrometer, but other detection methods can be used, as would be known to one skilled in the art. These include, but are not limited to laser measurement, infrared detection, nuclear magnetic resonance and liquid scintillation counting of labeled carbon.

The method of the invention can be used to detect bacterial overgrowth by comparing a standard in the form of the mean value of expired isotope in a normal population or a diseased population with the value(s) determined from the test subject. This test can be used in identifying the presence of bacterial overgrowth.

In the preferred embodiment, the individual is first required to fast overnight. This minimizes metabolic effects of meal absorption and the contribution of endogenous label appearing in the breath from natural levels of the endogenous isotope in the diet. However, the test may be conducted without requiring overnight fasting. Preferably at least two baseline samples (of breath and/or blood) are collected and the mean isotope value in these samples is used as a background. In an alternative embodiment, only one background measurement is made or, alternatively, no background measurement is made. If no background measurement is made, the amount of label in the specimen is taken as the measurement for comparison with a control value. If a background measurement is made, this background is subtracted from the labeled carbon levels determined following isotopic administration in order to obtain the change in labeled species level.

It is preferable to wait a sufficient amount of time after administration before collecting the sample(s) to allow metabolism of the labeled compound to release the labeled species. A sufficient amount of time is about 5 minutes to about 120 minutes, preferably about 10 minutes to about 90 minutes, and most preferably about 30 minutes to about 60 minutes.

Preferably, 1 to 1,000 mg of the compound are given to the test subject. More preferably, about 100 to about 300 mg are administered, and most preferably about 150 to about 250 mg of the compound are administered.

In one embodiment, the specimen is one or more breath samples. All breath samples, both those collected prior to administration of the isotope and those after administration, may be collected with a commercially available breath sampler. These include, but are not limited to a Quintron AlveoSampler (Milwaukee, Wis.). These samplers have a mouthpiece and a collection bag with a one-way valve there between. The breath samples are trapped in a collection bag or other suitable breath collection device and the contents are injected into an evacuated tube such as, but not limited to an Exetainer tube (Labco Ltd, U.K.).

Alternatively, the specimen may be one or more blood samples. All blood samples, both those collected prior to administration of the isotope and those after administration, may be collected with a commercially available blood collection device such as, but not limited to, a heparinized Vacutainer "butterfly" blood collection set (Vacutainer, Franklin Lakes, N.J.), a syringe, or a Vacutainer holder with an evacuated Vacutainer tube. Preferably, the blood specimen is venous blood, but arterial and/or capillary blood can also be tested. The blood sample collected is then preferably reacted with acid to liberate dissolved $CO_2$. Suitable acids include, but are not limited to, citric, phosphoric, hydrochloric and sulfuric acid. Preferably, the acid is citric acid. The ratio of saturated citric acid to specimen is preferably 0.01 to 0.5 (volume/volume), and most preferably 0.03 to 0.1 (volume/volume). The amount and type of acid to be added to the specimen can be determined by one of skill in the art. Addition of acid to the specimen is needed to generate a suitable headspace specimen having $CO_2$ for analysis. The headspace containing the labeled $CO_2$ is either sampled directly or transferred to an evacuated Exetainer tube (Labco Ltd, U.K.) or Vacutainer tube prior to analysis.

A schematic diagram outlining the mechanism of action of the sorbitol test is given in FIG. 1. Isotopically labeled sorbitol is taken orally and transported to the small bowel. In the presence of an overabundance of bacteria, sorbitol is appreciably metabolized to $CO_2$. The labeled $CO_2$ can be detected in the breath and blood of the patient. A positive indication is revealed by the degree to which the breath or blood is enriched by the isotopically labeled $CO_2$.

In one embodiment, the patient arrives at the testing site after an overnight fast. A baseline blood or breath sample is collected. Isotopically labeled sorbitol is dissolved in water and administered orally. Breath or blood samples are collected at regular intervals for several hours. Enrichment of $CO_2$ in breath or blood is measured using an isotope ratio mass spectrometer (for $^{13}$C), a scintillation counter (for $^{14}$C) or comparable device familiar to one skilled in the art.

The following examples serve to illustrate specific embodiments of the invention, but should not be considered as a limitation on the scope of the invention.

EXAMPLE

Sorbitol Breath Test

Methods:

Nineteen patients with symptoms suggestive of small bowel bacterial overgrowth (diarrhea, weight loss, bloating, and abdominal pain) were prospectively evaluated with jejunal cultures and non-invasive breath tests utilizing $^{14}$C-xylose, $^{13}$C-xylose, and $^{13}$C-sorbitol. Results are reported as percent of $^{14}$C or $^{13}$C recovered in exhaled $CO_2$. Jejunal cultures were obtained from three intestinal aspirates distal to the ligament of Treitz using standard methods. The culture was considered positive if the number of colonies of relevant species was $10^5$ or higher.

Breath tests were performed after an overnight fast. 150 milligrams of $^{14}$C-xylose or $^{13}$C-xylose or 200 milligrams $^{13}$C-sorbitol was dissolved in 250 milliliters water and ingested orally. Breath samples were collected at 30 minute intervals for 4 hours.

Results:

Nine of nineteen patients had positive jejunal cultures and were positive for small bowel bacterial overgrowth. The results for the breath tests compared to culture are presented in Table 1.

TABLE 1

|  | $^{14}$C-xylose | $^{13}$C-xylose | $^{13}$C-sorbitol |
| --- | --- | --- | --- |
| Sensitivity (%) | 56 | 67 | 89 |
| Specificity (%) | 39 | 40 | 40 |
| Positive Predictive Value (%) | 42 | 67 | 57 |
| Negative Predictive Value (%) | 43 | 40 | 80 |
| Accuracy (%) | 42 | 57 | 63 |

The results show that compared with jejunal cultures, the sensitivity and specificity of xylose based breath tests have decreased. The high sensitivity (89%), negative predictive value (80%), and accuracy (63%) support $^{13}$C-sorbitol breath test as a useful test for detecting small bowel bacterial overgrowth.

Many other variations and modifications may be made in the methods herein described, by those having experience in this art, without departing from the concept of the present invention. Accordingly, it should be clearly understood that the methods described in the foregoing description are illustrative only, and not intended as a limitation on the scope of the invention.

What is claimed is:

1. A method of assessing bacterial overgrowth in the small intestine of a subject comprising the steps of:

a. administering an amount of carbon-labeled sorbitol or sorbitol derivative to said subject, wherein said sorbitol derivative has the characteristics of not being readily absorbed by said subject and being metabolizable by bacteria;

b. collecting a specimnen from said subject;

c. measuring an amount of labeled carbon in said specimen to obtain a measured amount; and d. comparing said measured amount with a positive standard and a negative standard to assess bacterial overgrowth in said subject, wherein said negative standard is an amount of expired labeled carbon in a control group without bacterial overgrowth, and wherein said positive standard is an amount of expired labeled carbon in a control group with bacterial overgrowth.

2. The method according to claim 1 wherein said carbon-labeled sorbitol or sorbitol derivative is selected from the group consisting of $^{14}$C sorbitol or sorbitol derivative and $^{13}$C sorbitol or sorbitol derivative, or mixtures thereof.

3. The method according to claim 1 wherein said carbon-labeled sorbitol is $^{13}$C sorbitol.

4. The method according to claim 1 wherein said carbon-labeled sorbitol or sorbitol derivative is labeled at the 1-position of sorbitol or the 1-position of the sorbitol derivative.

5. The method of claim 1 wherein said carbon-labeled sorbitol or sorbitol derivative comprises a plurality of labeled carbons.

6. The method according to claim 1 wherein said labeled carbon in said specimen is labeled carbon dioxide.

7. The method according to claim 6 wherein said labeled carbon dioxide in said specimen is $^{13}$C carbon dioxide.

8. The method according to claim 1 wherein said administering step comprises administering carbon-labeled sorbitol or sorbitol derivative in a pharmaceutically acceptable carrier.

9. The method according to claim 1 wherein said measuring comprises isotopic measurement of labeled carbon.

10. The method according to claim 9 wherein said measurement is selected from the group consisting of mass spectrometric measurement, laser measurement, infrared detection, nuclear magnetic resonance and liquid scintillation counting of labeled carbon.

11. The method according to claim 1 wherein said specimen is selected from the group consisting of breath or blood.

12. The method according to claim 11 wherein said blood specimen is selected from the group consisting of venous, capillary and arterial blood.

13. The method according to claim 12 wherein said blood specimen is treated with an acid prior to analysis of $CO_2$.

14. The method of claim 1, wherein said carbon-labeled sorbitol derivative is sorbitol.

* * * * *